United States Patent [19]

Bhasin et al.

[11] 4,246,186

[45] Jan. 20, 1981

[54] PROCESS FOR PRODUCING ACETIC ACID, ETHANOL, AND ACETALDEHYDE FROM SYNTHESIS GAS

[75] Inventors: Madan M. Bhasin; George L. O'Connor, both of Charleston, W. Va.

[73] Assignee: Union Carbide Corporation, New York, N.Y.

[21] Appl. No.: 650,799

[22] Filed: Jan. 20, 1976

Related U.S. Application Data

[63] Continuation of Ser. No. 541,661, Jan. 16, 1975, abandoned, Continuation-in-part of Ser. No. 437,141, Jan. 28, 1974, abandoned.

[51] Int. Cl.$^3$ ............................................. C07C 27/06
[52] U.S. Cl. ................................................. 260/449 R
[58] Field of Search .................................... 260/449 R

[56] References Cited

PUBLICATIONS

Fischer et al., "Brenstoff-Chemie", 17, 265–284, (1925).
Fischer et al., "Brenstoff-Chemie", 16, 466, (1935).
Pichler, "Brenstoff-Chemie", 19, 226, (1939).
Kratel, Doctoral Dissertation, Technical University of Berlin-Charlattburg, (1937).
Eidus et al., Iquest. Akad. Navk, SSSR, Ser Khim., 7, 1160–1169, (1965).
Schultz et al., Bureau of Mines Report No. 6974.

Primary Examiner—Alan Siegel
Attorney, Agent, or Firm—Bernard Lieberman

[57] ABSTRACT

A process for the selective preparation of two-carbon atom oxygenated hydrocarbons, namely acetic acid, ethanol, and acetaldehyde, by continuously contacting a reaction mixture containing hydrogen and carbon monoxide with a rhodium metal catalyst, at a combination of reaction conditions correlated so as to favor the formation of a substantial proportion of these products.

6 Claims, No Drawings

PROCESS FOR PRODUCING ACETIC ACID, ETHANOL, AND ACETALDEHYDE FROM SYNTHESIS GAS

CROSS-REFERENCE TO RELATED APPLICATIONS

This is a continuation of our prior U.S. application Ser. No. 541,661 filed Jan. 16, 1975 now abandoned, which is a continuation in part of application Ser. No. 437,141 filed Jan. 28, 1974 now abandoned.

BACKGROUND

This invention concerns the selective preparation of two-carbon atom oxygenated hydrocarbons, namely acetic acid, ethanol, and/or acetaldehyde, from synthesis gas. More particularly, the invention concerns reaction of synthesis gas in the presence of a heterogeneous catalyst to produce such products.

The preparation of hydrocarbons and oxygenated hydrocarbons from synthesis gas (essentially a mixture of carbon monoxide with varying amounts of carbon dioxide and hydrogen) has received extensive study and has achieved commercial adoption. Reaction conditions generally involve temperatures on the order of 150°–450° C., pressures of from atmospheric to about 10,000 psig, and hydrogen-to-carbon monoxide ratios in the range of 4:1 to about 1:4, with an iron group or a noble metal group hydrogenation catalyst.

One serious disability of most synthesis gas processes has been the non-selective or non-specific nature of the product distribution. Catalysts which possess acceptable activity generally tend to give a wide spectrum of products—hydrocarbons and oxygenated hydrocarbons—having a broad distribution of carbon atom contents. This not only complicates the recovery of desired products, but results in the wastage of reactants to commercially uninteresting byproducts.

SUMMARY OF INVENTION

In accordance with the invention, a process is provided for the reaction of carbon monoxide with hydrogen to prepare, selectively, oxygenated hydrocarbons of two carbon atoms per molecule. Synthesis gas is continuously contacted with a catalyst essentially comprising rhodium metal, at a combination of reaction conditions correlated so as to favor the formation of a substantial proportion of acetic acid, ethanol, and/or acetaldehyde.

The reaction is conducted at reactive conditions of temperature, pressure, gas composition and space velocity correlated so as to collectively produce acetic acid, ethanol, and/or acetaldehyde in an amount which is at least about 50 weight percent, preferably at least about 75 weight percent, of the two and more carbon atom compounds obtained by the reaction. Desirably, the reaction is conducted at these correlated conditions to achieve product efficiencies based on carbon consumption in excess of 10%, and frequently in excess of 50%. Ethyl esters and acetates formed are included as ethanol and acetic acid in determining productivities and selectivities as used in data presented herein. At optimum reaction conditions, and particularly at relatively low conversions, there is little conversion to three carbon atom and higher hydrocarbons and oxygenated hydrocarbons, and conversion to methane and methanol may readily be minimized. As will appear, it is also possible, through variations in catalyst composition and reaction conditions, to direct the selectivity toward only one of the three products, e.g. acetic acid or ethanol.

RELATION TO PRIOR ART

The literature on synthesis gas conversion is extensive. While it is rare to find a metal that has not been investigated as a catalyst for the reaction, most efforts to date have focused on the iron group metals, on ruthenium, and on various metal oxide systems.

Extensive literature surveys have revealed that five prior workers have investigated the use of rhodium metal as a synthesis gas conversion catalyst. Their publications, identified in Table I below, report results which are no more impressive than are obtained with iron group catalysts. In view of these results and the relatively high price of rhodium, it is not surprising to find there has been so little interest in the use of rhodium as a catalyst for synthesis gas conversion.

TABLE I
COMPARISON TO PRIOR ART

| Author | Support | T, °C. | P, psi | $PH_2/PCO$ | RGV (6) | Mole % HAc + EtOH + HOAc |
|---|---|---|---|---|---|---|
| F. Fischer, et al (1) | None | 300–400 | 15 | 5 | 0.24 | None found |
| R. Kratel (2) | None | 195 | 1500 | 2 | ca.1.3 | Presume like Soufi |
| Eidus, et al (3) | Kieselguhr Alumina | 250–300 | 15–600 | 2–1 | 2.2 to 5.4 | Presume like Soufi |
| Bureau of Mines (4) | Alumina | 441 | 315 | 3 | 60. | None found |
| F. Soufi (5) | None | 140–220 | 3300–15,000 | 2 | 0. to ca. 0.2 | 0.14–3.37 |
| This invention | Various and None | 200–350 | 700–3500 | 3–.25 | ca 10. to 2000. | Up to about 80 |

(1) F. Fischer, et al., Brennstoff-Chemie, 16, 466 (1935); 6, 265–284 (1925).
(2) R. Kratel, Dissertation, Technical University of Berlin-Charlottenburg, 1937. Work done at Kaiser-Wilheim-Institute at Mulheim-Ruhr. (See also, H.Pichler, Brennstoff-Chemie, 19, 226 (1939).)
(3) Ya. T. Eidus, et al., Isvest. Akod. Nauk, SSSR, Ser. Khim., 7, 1160–1169 (1965).
(4) J. F. Schultz, et al., Bureau of Mines Report of Investigations No. 6974 (1967), (Cf. L. Duparc, et al., Helv. Chim. Acta, 8, 609(1925).)
(5) F. Soufi, Doctoral Dissertation, University of Karlsruhe (1969).
(6) RGV = Relative Gas Velocity. As used here, the relative gas velocity is the volume of synthesis gas, measured in liters at 1 atm. and 0° C., fed to the catalyst per gram of rhodium present per hour.

The relationship between reaction conditions employed and the results achieved by prior workers are well summarized in the above Table. None reported or found more than 3.4 mole percent of two carbon atom oxygenated compounds in the reaction products. This contrasts with as much as 80 mole percent two carbon atom oxygenated compounds in the presently described process. There is evidently an importance in associating a rhodium metal catalyst with correlated reaction conditions to favor the formation of a substantial proportion of acetic acid, ethanol, and/or acetaldehyde.

A more detailed illustration of the difference between Soufi's results and those obtained by the practice of the present invention is shown in Table II.

TABLE II

COMPARISON OF PRODUCT DISTRIBUTIONS

| Product | Wt. % Organic Products | |
|---|---|---|
| | Present Study | Soufi |
| methane | 33.6 | 17.4 |
| ethane | nil | 22.7 |
| acetaldehyde | 13.9 | 0.2 |
| ethanol | 4.7 | 0.5 |
| acetic acid | 23.6 | 0.5 |
| misc. $C_2$-$C_4$ hydrocarbons | trace | 36.4 |
| misc. C, and $C_3$-$C_6$ oxygenated hydrocarbons (a) | 0.5 | 17.6 |
| $CO_2$ | 23.8 | 4.7 |
| Conditions | | |
| Temperature (°C.) | 220° | 220° |
| Pressure (psig) | 3000 | 1500–3400 |
| $H_2$/CO | 2:1 | 2:1 |
| Space Velocity (V/hr./V)* | 1800 | static (8.5 hrs.) |
| Run Duration (hrs.) | 1 | 8.5 |
| Catalyst | 5% Rh°/$SiO_2$ | Rh° powder |

(a) aldehydes, acids & alcohols.
*Volume of gas per hour per volume of catalyst

DETAILED DESCRIPTION

In keeping with the invention, a synthesis gas containing carbon monoxide and hydrogen is contacted with a rhodium metal catalyst under reactive conditions of temperature, pressure, gas composition and space velocity correlated so as to favor as stated previously, the formation of a substantial proportion of acetic acid, ethanol, and/or acetaldehyde. The reaction efficiency, or selectivity, to these two-carbon atom compounds is invariably at least about 10%, and is usually upwards of about 25%; under the preferred conditions it exceeds 50% and, under optimum conditions, has reached 90% or more. Selectivity is defined herein as the percentage of carbon atoms converted from carbon monoxide to a specified compound or compounds other than $CO_2$.

Thus, the independent reaction variables are correlated so as to favor the formation of a substantial proportion of the desired two carbon atom oxygenated hydrocarbons (acetic acid, ethanol, and/or acetaldehyde). This proportion, expressed as carbon conversion efficiency, is usually upwards of 25% and frequently exceeds 50%.

In one aspect of the invention, this correlation is a combination of conditions which result in maintaining moderate reaction conditions to thereby limit the conversion of CO to not more than about one fourth, preferably not more than about one eighth. As will be discussed in detail below, this may be achieved primarily by a combination of high space velocity and low temperature, but other factors (e.g. $H_2$/CO ratio, catalyst activity, pressure, bed geometry, etc.) also affect the conversion. At high conversions, it has been noted that higher carbon number hydrocarbons and oxygenated hydrocarbons are produced in excess, with a resulting loss in efficiency to two-carbon atom compounds.

Conditions of temperature, of pressure, and of gas composition are usually within the ranges that are essentially conventional for synthesis gas conversions, particularly those employed in the production of methanol. Thus, existing technology and, in some instances, existing equipment may be used to effect the reaction.

The reaction is highly exothermic, with both the thermodynamic equilibrium and the kinetic reaction rates being governed by the reaction temperature. Average catalyst bed temperatures are usually within the range of about 150°–450° C., but for optimum conversions, bed temperatures are kept within the range of about 200°–400° C., typically about 250°–350° C.

The reaction temperature is an important process variable, affecting not only total productivity but selectivity toward one or more of the desired two carbon atom products. Over relatively narrow temperature ranges, as for example 10° or 20° C., an increase in temperature may somewhat increase total synthesis gas conversion, tending to increase the efficiency of ethanol production but decreases the efficiency of acetic acid and acetaldehyde production. At the same time, however, higher temperatures favor methane production, and apparently methane production increases much more rapidly at higher temperatures than do conversions to the more desirable two carbon atom products. Thus, for a given catalyst and with all other variables held constant, the optimum temperature will depend more on product and process economics than on thermodynamic or kinetic considerations, with higher temperatures tending to increase the production of oxygenated products but disproportionately increasing the co-production of methane.

In the discussions above the indicated temperatures are expressed as average, or mean, reaction bed temperatures. Because of the highly exothermic nature of the reaction, it is desirable that the temperature be controlled so as not to produce a runaway methanation, in which methane formation is increased with higher temperature, and the resulting exotherm increases the temperature further. To accomplish this, conventional temperature control techniques are utilized, as for example the use of fluidized bed reaction zones, the use of multistage fixed bed adiabatic reactors with interstage cooling, or relatively small (1/16th inch or less) catalyst particles placed in tube-and-shell type reactors with a coolant fluid surrounding the catalyst-filled tubes.

The reaction zone pressure is desirably within the range of about 15 psig to about 10,000 psig, economically within the range of about 300–5,000 psig. Higher reaction zone pressures increase the total weight of product obtained per unit time and likewise improve the selectivity toward two carbon atom compounds.

The ratio of hydrogen to carbon monoxide in the synthesis gas may vary widely. Normally the mole ratio of hydrogen to carbon monoxide is within the range of 20:1 to 1:20, or preferably within the range of about 5:1 to about 1:5. In most of the experimental work reported herein the mole ratio of the hydrogen to carbon monoxide is somewhat less than 1:1. Increasing the ratio tends to increase the total rate of reaction, sometimes quite significantly, and has a small but favorable effect on production of two carbon atom products, but concurrently increases selectivity to methane. Increasing the hydrogen to carbon monoxide ratio also favors the formation of more highly reduced products, that is, ethanol rather than acetaldehyde or acetic acid.

Impurities in the synthesis gas may or may not have an effect on the reaction, depending on their nature and concentration. Carbon dioxide, normally present in an amount of up to about 10 mole percent, has essentially no effect. If a recycle operation is conducted, in which all or part of the reacted gas is recycled to the catalyst zone, it is desirable to remove oxygenated hydrocarbons before recycling.

To provide empirical orientation, a set of ten experiments, in the form of a two-level, fractional factorial design plus centerpoints, was conducted. The independent variables were temperature (275° and 300° C.), hydrogen and carbon monoxide partial pressures (350 and 500 psig), and gas hourly space velocities (3600 and 4700 volumes of gas at standard conditions per volume of catalyst per hour). All variables, with the exception of space velocity, proved to be significant in their influences on the rates and efficiencies to the principal products, i.e., acetic acid, ethanol, acetaldehyde, and methane. (Note, however, that space velocity was varied over a comparatively narrow range, and in each instance was quite high.) Qualitatively, these responses are indicated in Table III below. In each instance, the effect of an increase in the specified variable is represented by either one or more positive or negative signs to characterize the degree of response of the rate and/or of the efficiency.

TABLE III

| | Rate | | | Efficiency | | |
|---|---|---|---|---|---|---|
| | Temp. | $PH_2$ | PCO | Temp. | $PH_2$ | PCO |
| Acetic Acid ($CH_3COOH$) | + | + | ++ | --- | − | +++ |
| Ethanol ($C_2H_5OH$) | ++ | ++ | − | ++ | + | − |
| Acetaldehyde ($CH_3COH$) | + | + | + | -- | − | + |
| Methane ($CH_4$) | +++ | + | − | +++ | ++ | --- |

The results of Table III, above, suggest that the conditions most favorable to high selectivity toward acetic acid and acetaldehyde are the lowest practical operating temperaure, low hydrogen partial pressure, and high carbon monoxide partial pressure. Verification of this prediction is provided in the following data (here and in Table III utilizing a 5% rhodium on silica catalyst) presented in Table IV below.

TABLE IV
Effects of Temperature, Pressure, and Gas Composition

| | | | Carbon Efficiency, % | | | | Productivity (a) | |
|---|---|---|---|---|---|---|---|---|
| Temp. | $PH_2$ | PCO | Methane | Acetic Acid | Ethanol | Acetaldehyde | Acetic Acid | Total to $C_2$'s |
| 290 | 425 | 425 | 35 | 18 | 12 | 29 | 4.0 | 10.7 |
| 275 | 250 | 500 | 20 | 33 | 10 | 34 | 2.4 | 4.8 |
| 250 | 750 | 1750 | 11 | 34 | 10 | 45 | 1.4 | 3.0 |

(a) Lbs. of Product/Cubic feet of catalyst/Hr.

One of the features of the present invention is the recognition that a low conversion--preferably less than 20% of the CO--favors the formation or production of a substantial proportion of acetic acid, ethanol and/or acetaldehyde, generally in excess of 10% as compared with a maximum of 3.4% in the prior art (Table I). This conversion is conveniently achieved by employing a high space velocity correlated with other reaction variables (e.g. temperature, pressure, gas composition, catalyst, etc.). Space velocities in excess of about $10^3$ gas hourly space velocity (volumes of reactant gas, at 0° C. and 760 mm mercury pressure, per volume of catalysts per hour) are generally employed, although it is preferable that the space velocity be within the range of about $10^4$ to about $10^6$ per hour. Excessively high space velocity result in an uneconomically low conversion, while excessively low space velocities cause the production of a more diverse spectrum of reaction products, including higher boiling hydrocarbons and oxygenated hydrocarbons.

The rhodium catalyst is rhodium metal provided in the reaction zone by a number of techniques, or a combination of a number of these techniques. One technique is to coat the reaction zone (or reactor) walls with rhodium metal. Another is to coat a porous screen or screens with a thin coating of the metal. Still another way involves placing particles of rhodium in the reaction zone, generally supported by an inert porous packing material. Another way is to deposit rhodium onto a particulate support material and place the supported rhodium into the reaction zone. Any combination of these techniques can be employed.

However, important advantages within the scope of the invention are achieved when the rhodium metal catalyst is in a highly dispersed form on a particulate support. On the basis of experience to date the amount of catalysts on the support should range from about 0.01 weight percent to about 25 weight percent, based on the combined weight of the metal catalyst and the support material. Preferably, the amount of catalyst is within the range of about 0.1 to about 10 weight percent.

A wide variety of support materials has been tested. A relatively high surface area particulate support, e.g. one having a surface area upwards of about 1.0 square meters per gram (BET low temperature nitrogen adsorption isotherm method), is preferred, desirably upwards of about 1.5 square meters per gram, although surface area alone is not the sole determinative variable. Based on research to date, silica gel is preferred as the catalyst base or support, with alpha alumina, magnesia, eta alumina, gamma alumina, and active carbon being progressively less desirable. Zeolitic molecular sieves, primarily the higher silica-to-alumina crystalline zeolites, also have promise.

The rhodium metal may be deposited onto the base or support by any of the techniques commonly used for catalyst preparation, as for example impregnation from an organic or inorganic solution, precipitation, copre- cipitation, or cation exchange (on a zeolite). Numerous specific embodiments of catalysts preparatory techniques are described in the Examples below; it suffices for the present to say that an inorganic or organic rhodium compound is appropriately contacted with the support material, and the support then dried and heated, the latter advantageously under reducing conditions, to form the finely dispersed rhodium metal.

The invention in its various aspects is illustrated in the different "Series" of experiments presented below. In each instance it will be appreciated that the tests are exemplary only, and are not intended to be wholly definitive or exclusive with respect to scope or conditions of the invention.

SERIES A

This Series illustrates the preparation and testing of supported rhodium metal catalysts on a variety of high surface area supports. It also contrasts supported rhodium with supported iridium, supported ruthenium, supported palladium, supported platinum, supported copper, and supported cobalt.

Preparation of Catalysts

Catalysts tested in this study were all prepared by essentially the same sequence of steps: An aqueous solution of the desired component was impregnated on the support; the impregnated support was carefully dried; the metal salt was reduced slowly in a flowing hydrogen atmosphere. When metal components were impregnated as nitrate salts, a pyrolysis step preceeded the hydrogen reduction step. In most cases, rhodium was impregnated as a $RhCl_3$ solution.

The description below illustrates this procedure for the catalyst used in Tests 1-7 (5% rhodium on Davison TM Grade 59 Silica Gel). Table V summarized preparative details for the catalysts whose activities are described in this Series.

Rhodium trichloride (22.58 gm, 41.93% Rh) was dissolved in 240 ml of distilled water at ambient temperature. Davison TM Grade 59 silica gel (200.0 gm, 3-6 mesh) was placed in a vacuum flask. The top of the flask was sealed with a rubber septum, and the flask was evacuated through the side arm. A syringe needle was then used to inject the rhodium solution onto the evacuated support. When addition was complete, the impregnated support was allowed to stand at one atmosphere for ca. 30 minutes. It was then carefully dried in a nitrogen atmosphere: 80° C. (1 hr); 110° C. (2 hrs); 150° C. (2 hrs). The dried, impregnated support was placed in a quartz tube through which hydrogen was continuously passed. The temperature was raised to 450° C. and held at that value for 2 hours. The reduced catalyst was cooled to ambient temperature in an atmosphere of flowing nitrogen.

The following modifications were found to facilitate operation and inhibit run-away methanation reactions.

1. Hydrogen feed gas was introduced continuously at the bottom of the autoclave through the well for the shaft of the Magnedrive agitator.
2. Carbon monoxide feed gas was introduced continuously through a separate port at the bottom of the autoclave, in order to avoid a hydrogen-rich zone in the autoclave. When carbon dioxide was fed, it was added with the carbon monoxide feed stream.

Experimental

Rhodium catalysts supported on silica gel, gamma-$Al_2O_3$, and carbon were tested for synthesis activity in a backmixed autoclave described above. Reaction conditions and salient features of the product distribution are described in Table VI below. In all cases, the feed gases included a quantity of carbon dioxide; the nominal level of carbon dioxide in the feed was 5% by volume, but the actual feed rates achieved probably varied widely from this value. There was no indication that carbon dioxide had any effect on the activity or selectivity of any of the catalysts studied.

Under the conditions of these studies, rhodium catalysts supported on silica gel had a selective activity for production of two-carbon, oxygenated compounds. Carbon efficiency data are given for ethanol and acetic acid. Methyl-, ethyl-, and propyl-acetate esters are also formed. (Other work had shown that acetaldehyde was also produced by these catalysts. Acetaldehyde production was very poorly reflected in the results reported here, because the analytical system did not distinguish acetaldehyde from methanol.) A number of relatively

TABLE V

DESCRIPTIONS OF CATALYSTS STUDIED

| Test No. | Metal, %'s | Support | Dispersion, % | Metal Origin(s) |
|---|---|---|---|---|
| 1–7 | Rh (5%) | Davison 59 Silica Gel | 22. | $RhCl_3$ |
| 8–11 | Rh (2.5%) | Norton LA 6173 | 58. | $RhCl_3$ |
| 12 | Rh (5%) | Pittsburgh Carbon | 77. | Matthey-Bishop Catalyst |
| 13, 14 | Rh (2.5%) | Norton LA 6173 | 86. | $RhCl_3$ |
| 15, 16 | Rh (2.5%) | Davison 59 Silica Gel | 21. | $Rh(NO_3)_3$ |
| 17, 18 | Ir (2.75%) | Davison 59 Silica Gel | 30. | $IrCl_4$ |
| 19, 21 | Ru (5%) | Davison 59 Silica Gel | 11. | $RuCl_3 \cdot H_2O$ |
| 22 | Pd (5%) | Davison 59 Silica Gel | 9.9 | Pd (acetyl/lacetonate)$_2$ |
| 23 | Pt (5%) | Davison 59 Silica Gel | 11. | $H_2PtCl_4(aq)$ |
| 24 | Cu (0.65%) | Davison 59 Silica Gel | — | $Cu(O_2CCH_3)_2 + NH_3(aq)$ |
| 25 | Co (2.5%) | Davison 59 Silica Gel | — | $[Co(H_2O)_6]Cl_2$ |

Description of Test Reactor

The reactor used in these studies was a bottom-agitated "Magnedrive" autoclave of the J. M. Berty design with a centrally positioned catalyst basket and a side product effluent line. It is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology—Part II, Sixty Fourth National Meeting of the American Institute of Chemical Engineers (AIChE), at New Orleans, Louisiana, on Mar. 16-20, 1969 and obtainable from AIChE at 345 East 47 Street, New York, N.Y. 10017. A variable speed, magnetically driven, fan continuously recirculated the reaction mixture over the catalyst bed.

minor products were also formed. These included methanol, propanol, and propanal. The major inefficiency in these syntheses was methane.

Those rhodium catalysts for which the support was gamma-$Al_2O_3$ or carbon also showed significant selectivities to ethanol and acetic acid. However, these catalysts were much less active than silica gel supported catalysts at closely similar reaction conditions, despite the fact that the Rh dispersion was much higher.

A brief study of the RPM of the fan in the backmixed autoclave was made in Tests 1–4 to determine the effect of RPM on productivity. Dropping RPM from 1500 to 750 did not affect the productivity; however, decreasing RPM to 400 did decrease the productivity. An RPM of 800 was used in all later work.

TABLE VI

SYNTHESIS GAS TO CHEMICALS OVER SUPPORTED METAL CATALYSTS

| Test | Catalyst | GHSV hr$^1$ (h) | T, °C. | P psig | % CO | CH$_4$ | CH$_3$OH | C$^{(a)}$ Eff. (%) Ethanol | Acetic Acid | Rate to C$_2$ Products, lb/cf/hr |
|---|---|---|---|---|---|---|---|---|---|---|
| 1 | 5% Rh/SiO$_2$ | 2200 | 325 | 2500 | 72. | 37. | 7.4 | 33. | 18. | 2.1(b) |
| 2 | 5% Rh/SiO$_2$ | 2100 | 325 | 2500 | 74. | 41. | 5.9 | 30. | 18. | 2.5(c) |
| 3 | 5% Rh/SiO$_2$ | 1700 | 325 | 2500 | 75. | 47. | 4.6 | 26. | 18. | 0.95(d) |
| 4 | 5% Rh/SiO$_2$ | 2000 | 325 | 2500 | 69. | 50. | 3.7 | 26. | 14. | 1.4(e) |
| 5 | 5% Rh/SiO$_2$ | 5400 | 325 | 2500 | 76. | 18. | 13. | 16. | 45. | 22.(g) |
| 6 | 5% Rh/SiO$_2$ | 8000 | 325 | 2500 | 77. | 24. | 10. | 20. | 38. | 19. |
| 7 | 5% Rh/SiO$_2$ | 10,000 | 325 | 2500 | 78. | 48. | 1.2 | 11. | 39. | 2. |
| 8 | 2.5% Rh/gamma-Al$_2$O$_3$ | 4900 | 250 | 2500 | 67. | 59. | 2.4 | 15. | 22. | 0.23 |
| 9 | 2.5% Rh/gamma-Al$_2$O$_3$ | 5100 | 300 | 2500 | 71. | 41.(f) | 5.6 | 12. | 40 | 0.19 |
| 10 | 2.5% Rh/gamma-Al$_2$O$_3$ | 6400 | 325 | 2500 | 81. | 83. | 0.5 | 0.82 | 6.1 | 0.074 |
| 11 | 2.5% Rh/gamma-Al$_2$O$_3$ | 5800 | 350 | 2500 | 75. | 71. | 0.2 | 0.26 | 2.6 | 0.050 |
| 12 | 5% Rh/Carbon | 5800 | 250 | 2500 | 78. | 91. | 0.8 | 0.82 | 7.8 | 0.078 |
| 13 | 2.5% Rh/gamma-Al$_2$O$_3$ | 9500 | 325 | 2500 | 80. | 95. | 1.2 | 0.26 | 3.4 | 0.041 |
| 14 | 2.5% Rh/gamma-Al$_2$O$_3$ | 9500 | 325 | 2500 | 75. | 94. | 1.2 | 0 | 5.0 | 0.026 |
| 15 | 2.5% Rh/SiO$_2$ | 11,000 | 325 | 2500 | 74. | 41. | 1.6 | 5.2 | 49. | 4.2 |
| 16 | 2.5% Rh/SiO$_2$ | 11,000 | 325 | 2500 | 80. | 26. | 1.6 | 10. | 45. | 2.8 |
| 17 | 2.75% Ir/SiO$_2$ | 12,000 | 325 | 2500 | 79. | 97. | 0 | 0.02 | 2.8 | 0.009 |
| 18 | 2.75% Ir/SiO$_2$ | 8800 | 325 | 2500 | 74. | (m) | 2.2 | 9.4 | 82. | 0.12 |
| 19 | 5.0% Ru/SiO$_2$ | 6600 | 325 | 2500 | 82. | 78. | 2.8 | 5.6 | 7.3 | 0.50(i) |
| 20 | 5.0% Ru/SiO$_2$ | 10,000 | 275 | 2500 | 83. | 96. | 0.75 | 0.25 | 1.7 | 0.029(i) |
| 21 | 5.0% Ru/SiO$_2$ | 11,000 | 250 | 2500 | 83. | 96. | 0.63 | 0.66 | 1.8 | 0.13(i) |
| 22 | 5.0% Pd/SiO$_2$ | 8800 | 325 | 2500 | 78. | 11. | 88. | 0.52 | 0.52 | 0.017(j) |
| 23 | 5.0% Pt/SiO$_2$ | 8800 | 325 | 2500 | 74. | 0. | 100. | 0 | 0 | 0(k,1) |
| 24 | 0.65% Cu/SiO$_2$ | 9000 | 325 | 2500 | 85. | 98. | 2.3 | 0.01 | 0.17 | 0.001(l) |
| 25 | 2.5% Co/SiO$_2$ | 11,000 | 325 | 2500 | 75. | 97. | 0.1 | 0.09 | 3.0 | 0.038 |

Footnotes
(a)After complete hydrolysis of all ester products. The analytical method in use did not distinguish between acetaldehyde and methanol.
(b)Fan operated at 1500 rpm.
(c)Fan operated at 750 rpm.
(d)Fan operated at 400 rpm.
(e)Fan operated at 750 rpm.
(f)Ethane. Gas analysis questionable.
(g)This run was made with minimum start-up time to prevent contamination of rhodium catalyst by Fe or S.
(h)Approximate GHSV; vol. gas at ambient temperature and pressure per vol.catalyst per hour.
(i)The ruthenium catalyst also produced large quantities of water-insoluble, malodorous oil.
(j)The palladium on silica gel catalyst appeared to be an efficient methanol catalyst: carbon efficiency to methanol, 88%; rate of methanol production, 2.8 lb/cf/hr. See footnote (a).
(k)The platinum on silica gel catalyst appeared to be an efficient methanol catalyst. The only products detected were methanol and water. Rate of methanol production, 0.32 lb/cf/hr. Doubtless the analytical date for this experiment are seriously incomplete. See footnote (a).
(l)Liquid sample was a "prerun"; that is, it includes liquid collected during the time the reactor was being brought to the indicated conditions.
(m)Methane analysis not available. For this reason, the high efficiency to acetic acid calculated is undoubtedly an artifact.

Table VI also reports data on iridium, ruthenium, palladium, platinum, copper, and cobalt catalysts supported on silica gel. Testing of these catalysts was carried out under substantially the same conditions described above for the rhodium catalysts. Although two-carbon products were detected, in no case was the productivity comparable to that observed with rhodium catalysts.

The iridium catalyst was very inactive. Under the conditions used, it produced primarily methane.

The ruthenium catalyst was active, but it produced large quantities of hydrocarbon oil. This oil production was not surprising; an extensive literature has documented the use of ruthenium catalysts for synthesis of high molecular weight hydrocarbons. The results of Table VI reflect the analysis of the gaseous and aqueous layer products only.

The copper catalyst was inactive under these conditions.

The cobalt catalyst produced methane as the major product.

The data obtained for the platinum and palladium catalysts showed only very low activity for two-carbon products. These data were of low quality.

SERIES B

This Series illustrates the preparation and testing of a group of supported rhodium metal catalysts, employing a variety of rhodium compounds and catalyst supports. In the tests, the reaction was carried out in a one gallon Berty autoclave.

The procedure described below was used in Tests 1-15 recited in Table VII below. The carbon monoxide used contained a few percent carbon dioxide. It and the hydrogen were fed to the reactor in the desired molar ratio from 4,500 psig headers. The carbon monoxide stream to the reactor was purified in all but tests 1-4, inclusive, using ⅛ inch activated carbon pellets which had been dried at 250° C. in a nitrogen flow overnight.

One hundred eighty milliliters (ml) of catalyst were placed in the reactor in a perforated basket having a capacity of approximately 200 ml. The reactor was pressurized with hydrogen to 2,000 psig and the flows of carbon monoxide and hydrogen were adjusted to achieve the desired composition. During the pressurization of the reactor, the reactor temperature was adjusted to approximately 25° C. below that desired for that particular run.

The pressure was then raised to 2500 psig and the temperature raised to the desired reaction temperature. Approximately one hour was allowed for the reactor to come to a steady state before beginning to measure actual time of reaction. After one hour of reaction, a sample of liquid product was collected by cooling the product-containing gas through a brine condenser and then trapping the liquid product in a series of four traps having a capacity of approximately one liter per trap. The traps were maintained in a low temperature bath containing a mixture of dry-ice and acetone. The liquid products from all the traps and the condenser were then combined to obtain a single liquid sample, which was then analyzed and the results reported in the Table below. The non-condensable gases were metered through a wet-test meter to determine the volume of gas, and a gas sample was collected to determine its composition.

After the desired time of reaction, the reactor was shut down overnight and the catalyst maintained under a slight hydrogen flow at 600 psig. When testing was resumed the following day, the reactor was again brought to the selected set of reaction conditions in the manner described previously. Therefore the catalyst of Test 1 was stored overnight in hydrogen and then used the following day under the reaction conditions of Test 2, then stored overnight under hydrogen, and used the following day for Test 3 and the same procedure repeated through Test 4. The period for the reaction of the examples was one hour except for Tests 9 and 11 where the reactions in Tests 8 and 10 respectively, were allowed to continue three additional hours before a second sample was taken. The fourth hour sample of Tests 8 and 10 are reported as Tests 9 and 11 respectively.

The following illustrate the preparation and compositions of the catalysts used in the Table below.

Catalyst A

Three grams of rhodium carbonyl acetylacetonate were dissolved in 66 ml of toluene preheated to about 50° C. The toluene-catalyst solution was added to 200 grams of an alpha-alumina support in the form of ⅛-inch cylindrical pellets having a surface area characteristic of about 3.5 square meters/gram (m²/gm.) The alpha-alumina support was prepared by heating CONOCO$^{TM}$ N-alumina, obtained from Continental Oil Co. of New York, N.Y., to 1,200° C. for about 24 hours. The toluene was evaporated from the impregnated support by drying in a nitrogen purged oven at 100° C.

After removing the toluene, the impregnated support was heated to 150° C. and the temperature held therefor 1½ hours. The impregnated support was then oxidized by air at 500° C. in a tubular furnace for a sufficient time to remove any remaining organic residue from the catalyst. The oxidized catalyst was then reduced in the presence of hydrogen at 300° C. to yield a catalyst having a metal dispersion characteristic of 3.4 percent. (Although 0.6 percent rhodium is the intended metal composition of the finished catalyst, the actual metal dispersion may be somewhat higher and the total metal content proportionately lower depending upon the fraction of rhodium lost during the decomposition step by partial vaporization of the rhodium carbonyl acetylacetonate. Therefore, the metal composition of the finished catalyst is very likely somewhere on the order of 0.5 percent rather than the intended 0.6 percent.)

Catalyst B

The equipment and techniques used in this preparation were the same as those used in the preparation of Catalyst A, except that the metal salt rhodium chloride, RhCl$_3$.3H$_2$O, containing 41.4 weight percent rhodium, was used in place of the rhodium carbonyl acetylacetonate used in making Catalyst A. About 3.1 grams of the rhodium chloride salt were dissolved in approximately 66 ml of distilled water at room temperature. Inasmuch as the rhodium chloride completely dissolved in the water, there was no need to preheat the water or the support. Impregnation of the support was done as previously described in the making of Catalyst A. The support used was a commercially available alpha-alumina (AL-3920) from Harshaw Chemical Company of Cleveland, Ohio of 3/16 inch size and cylindrical shape, having a surface area of approximately 5 m²/g. The impregnated support was then dried in three successive stages: 85° C. for two hours, 200° C. for two hours. The impregnated support was then heated in air at 500° C. for two hours and reduced at 500° C. in hydrogen for 1.5 hours. The catalyst showed no loss of rhodium metal, which is believed due to the use of the inorganic rhodium salt. The finished catalyst had a rhodium metal concentration of about 0.6 percent.

Catalyst C

This involved the use of the rhodium organic salt of Catalyst A on the Harshaw alpha-alumina support of Catalyst B. The preparation procedure was the same as that used in Catalyst A except that the mixture was reduced, after the oxidation step, at 500° C. for two hours before charging it to the reactor. The finished catalyst showed a percent dispersion of 7.5 percent and a rhodium content of 0.6 percent.

Catalyst D 12.46 grams of the metal salt rhodium chloride was dissolved in 120 ml of distilled water at room temperature. This solution was then used to impregnate 100 gms. of Davison$^{TM}$, grade 59, silica gel, obtained from Davison Chemical Co. of Baltimore, Maryland. The support was then dried sequentially, at 80° C. for 1½ hours, 110° C. for 1.5 hours, and 150° C. for 3.0 hours. The dried, impregnated support was then heated at 400° C. for two hours, cooled in air at 100° C., and then heated in hydrogen up to 300° C. for 3.0 hours. The finished catalyst had a rhodium content of 5 percent on the Davison$^{TM}$, grade 59, silica gel and a percent dispersion of 15.6 percent.

Catalyst E

This involved the use of the rhodium organic salt of Catalyst A on the silica gel support of Catalyst D. The preparation and procedure used are the same as that used in Catalyst A except that the impregnated support was dried at 105° C. for 2.5 hours and then heated immediately to 150° C. for 3 hours. The dried, impregnated support was then oxidized at 500° C. for 1.5 hours and reduced in the presence of hydrogen at 500° C. for 1.5 hours. The finished catalyst should have a rhodium content of 0.6 percent on Davison$^{TM}$, grade 59, silica gel and a percent metal dispersion of 15.3 percent.

TABLE VII

| Test No. | Catalyst | T. °C. | Wt. of Catalyst | Percent[a] Dispersion | Feed Gas Composition %CO | Feed Gas Composition %CO$_2$ (in H$_2$) | Yield of Products (in grams) | | | | | | | | | |
|---|---|---|---|---|---|---|---|---|---|---|---|---|---|---|---|---|
| | | | | | | | Methane | Ethane | Water | Methanol | Acetaldehyde | Ethanol | Isopropanol | Methyl Acetate | Acetic Acid | Ethyl Acetate | n-Propanol | Other Organic Compounds |

| Test No. | Catalyst | T. °C. | Wt. of Catalyst | Percent[a] Dispersion | %CO | %CO$_2$ | Methane | Ethane | Water | Methanol | Acetaldehyde | Ethanol | Isopropanol | Methyl Acetate | Acetic Acid | Ethyl Acetate | n-Propanol | Other Organic Compounds |
|---|---|---|---|---|---|---|---|---|---|---|---|---|---|---|---|---|---|---|
| 1 | A | 300 | 176 | 3.4 | 25.0 | 1.57 | 5.23 | N.A. | 4.90 | 0.20 | 0.00 | 0.43 | 0.04 | 0.01 | 0.13 | 0.01 | 0.02 | 0.00 |
| 2 | A | 340 | 176 | 3.4 | 25.0 | 0.65 | 10.66 | 1.2 | 13.18 | 1.42 | 0.00 | 1.53 | 0.00 | 0.07 | 0.01 | 0.02 | 0.11 | 0.01 |
| 3 | A | 325 | 176 | 3.4 | 46.0 | 0.78 | 4.99 | 0.31 | 6.89 | 0.46 | 0.00 | 1.10 | 0.00 | 0.04 | 0.19 | 0.05 | 0.04 | 0.02 |
| 4 | A | 350 | 176 | 3.4 | 63.0 | N.A.[c] | 4.08 | N.A. | 6.59 | 0.55 | N.A. | 0.7 | N.A. | N.A. | 0.23 | N.A. | N.A. | N.A. |
| 5 | B | 350 | 165 | 12.5 | 22.0 | 0.05 | 22.64 | 5.44 | 27.59 | 4.68 | 0.02 | 3.24 | 0.00 | 0.12 | 0.0 | 0.02 | 0.86 | 0.22 |
| 6 | C | 350 | 180 | 7.5 | 47.0 | 3.51 | 13.27 | 0.56 | 15.84 | 0.52 | 0.10 | 2.23 | 0.0 | 0.06 | 0.36 | 0.17 | 0.08 | 0.05 |
| 7 | D | 350 | 59 | 15.6 | 23.0 | 1.09 | 112.7 | 2.71 | 101.32 | 1.12 | 0.46 | 5.37 | 0.0 | 0.07 | 0.02 | 0.04 | 0.0 | 0.00 |
| 8 | D | 350 | 59 | 15.6 | 24.0 | 0.85 | 63.42 | ~0.5 | 48.92 | 1.15 | 0.22 | 5.82 | 0.0 | 0.00 | 0.68 | 0.27 | 0.07 | 1.29 |
| 9 | D | 350 | 59 | 15.6 | 23.0 | 0.05 | 30.69 | ~0.5 | 36.05 | 2.60 | 0.42 | 15.57 | 0.0 | 0.17 | 1.49 | 0.80 | 0.48 | 0.23 |
| 10 | D | 350 | 59 | 15.6 | 77.0 | 1.87 | 9.29 | ~0.5 | 11.25 | 0.13 | 0.21 | 2.16 | 0.0 | 0.05 | 4.18 | 0.70 | 0.0 | 0.14 |
| 11 | D | 350 | 59 | 15.6 | 75.0 | 1.63 | 4.69 | ~0.5 | 8.17 | 0.29 | 0.41 | 4.06 | 0.0 | 0.24 | 5.14 | 1.95 | 0.0 | 1.17 |
| 12 | E | 350 | 59 | 15.3 | 25.0 | 0.97 | 4.4 | N.A. | 2.21 | 0.41 | 0.01 | 0.04 | 0.0 | 0.02 | 0.05 | 0.01 | 0.0 | 0.0 |

[a]Percent Dispersion as defined in text on page 33.
[b]Other organic compounds are primarily n-butanol, n-propyl acetate, n-butyl acetate.
[c]N.A. - where used in this table means "not analyzed".
*In Examples 1-4, the CO feed gas was not purified with the activated carbon traps.

Percent metal dispersion, as used herein, is defined as the percentage of metal atoms exposed on the catalyst surface as compared to the total number of metal atoms deposited. The percent metal dispersion was obtained by determining the chemisorption of carbon monoxide at room temperature on a clean metal catalyst surface, and then calculating the number of exposed surface atoms by assuming that one carbon monoxide molecule is chemisorbed per surface metal atom. These analytical procedures can be found in S. J. Gregg and K. S. W. Sing, *Adsorption Surface Area And Porosity,* where CO adsorption is described at pages 263-267 and the dynamic gas chromatographic technique is described at pages 339-343. The surface purity of the catalyst was measured by Auger Spectroscopic Analysis. The analysis of product and unreacted gases was accomplished by the use of gas chromatographic analysis of the various liquids and gases.

Tests 1 through 12 of Table VII were conducted at an early investigative stage of the present invention when reproduceability of metal catalyst activity was a problem. Auger Spectroscopic Analysis of the various fresh and used catalysts of the examples indicated that the inability consistently to produce a particular product distribution could be attributed to the presence of iron and/or nickel impurities on the surface of the used catalyst. There is no direct evidence that iron and/or nickel impurities preferentially attached themselves to the surface of the metal catalyst; however, it appears to be highly probable that this did occur. For example, the use of argon ion sputtering of an impure catalyst indicated that as the iron signal decreased several fold the rhodium signal increased somewhat. If the iron did in fact attach itself to the surface of the metal catalyst, it very likely would be in the form of iron metal or iron oxide as a result of its reaction with water. The presence of iron on the metal surface would explain the low values of rhodium dispersion measured by carbon monoxide chemisorption. Inasmuch as iron and nickel are known methanation catalysts, this could possibly account for the high amount of methane found in some of the examples. Installation of activated carbon traps in the carbon monoxide feed gas stream helped reduce the amount of iron and nickel present during the reaction.

The effect of increasing reaction temperature, studied in Tests 1 through 4 of Table VII was to increase overall productivity, to increase methane formation, and to increase the ratio of ethanol to methanol obtained while the ratio of the yield to acetic acid plus acetates remained about constant.

Changing the source of the rhodium on the catalyst support from carbonyl acetylacetonate to rhodium chloride did not alter the product spectrum nor did it appear to affect the level of conversion of products as illustrated by Tests 5 and 6 in Table VII. The lower overall activity of the catalyst derived from rhodium carbonyl acetylacetonate can be explained in terms of its lower dispersion and/or lower rhodium metal content. The lower yield of acetates in the rhodium chloride preparation run is primarily due to the lower partial pressure of carbon monoxide, which tends to favor the production of ethanol over acetic acid and acetates.

Increasing the rhodium concentration from 0.6 percent to 5 percent on the support increased the reaction rate and the product yield.

The effect of carbon monoxide and hydrogen partial pressures and of catalyst aging are illustrated in Tests 7 through 11. The tests show that a high ratio of carbon monoxide to hydrogen favors the formation of acetic acid while a low ratio of carbon monoxide to hydrogen favors the formation of ethanol. Production of higher alcohols was minimal in both cases. Increasing the partial pressure of carbon monoxide from 25% to approximately 75% decreased methane formation while increasing the yield of total acetic acid and acetates substantially. Carbon efficiency to useful liquid products at high carbon monoxide partial pressures (75%) was about 64% while carbon efficiency at low carbon monoxide partial pressures (25%) was about 35% as shown in Tests 7 through 11.

It can be seen from Tests 8, 9 and 12 that the activities of catalysts containing different levels of rhodium but having similar metal dispersions increase as the amount of rhodium present increases.

SERIES C

This Series illustrates the effects of reaction temperature and catalyst age on product distribution.

The same procedure and equipment used for the tests in Table VII were used for all the tests in Table VIII except for the following conditions which were held constant; the pressure was 2500 psia; feed gas composition was 77% volume CO, 20% H₂ and 3% CO₂; reactant feed rate was 600 liters/hour; and there was a one (1) hour reaction time.

The catalyst used in Tests 16 through 33 of Table VII was Catalyst D, above, i.e., rhodium, at a concentration of 5 percent, on a Davison ™, grade 59, silica gel support. In Table VIII, after tests 18 and 21, the catalyst was stored overnight at 250° C. in a 600 psig carbon monoxide atmosphere. After Test 23, the catalyst was stored for two days at 285° C. in a 2000 psig carbon monoxide atmosphere. After Test 26, the catalyst was stored overnight at 300° C. in a 600 psig hydrogen atmosphere. The catalysts used in Tests 16 and 29 are freshly prepared and were then reduced with hydrogen in the reactor before the reaction was commenced. The catalyst used in each test, other than for Tests 16 and 29, was obtained from the preceeding test.

The results reports in Table VIII indicate a substantial shift in catalyst performance as time progressed. The catalyst became more selective to the production of ethanol and less selective toward methane production with age. The molar ratio of acetic acid to ethanol produced decreased from a high of 63 in Test 16 to less than one (1) in Tests 24 through 28. This change in catalyst selectivity can perhaps best be explained by the presence of iron found in the recovered catalyst. Surface iron of 1.2 atomic percent was detected by Auger atomic analysis on the recovered catalyst of Test 28 while no iron was detected on the unused catalyst. The atomic percent ratio of rhodium to iron for the used catalyst of Test 28 was 12.2. The atomic percent ratio of Rh to Fe for the used catalyst from Test 33 was 40. The iron contamination probably arises through the generation of iron carbonyl from the reactor walls and its subsequent decomposition on the catalyst surface. This suggests that by purposely contaminating the catalyst with iron one provides a process which favors ethanol production.

The decrease in methane production in the results reported in Table VIII as compared with that of Table VII is perhaps due to the absence of nickel on the surface of the catalysts of Table VIII.

SERIES D

A series of studies were designed to determine the effect of space velocity on the product distribution over rhodium catalysts. These experiments were directed toward the more inclusive goal of a better definition of the reasons for the differences between the process of this invention and descriptions in the prior art.

Modifications to the reactant gas feed system to the Berty reactor permitted operation in a well-controlled manner at space velocities of about 400–500 hr$^{-1}$. Most previous experimentations had been with space velocities in the range of 800–3000 hr$^{-1}$.

Additionally, it was found possible to operate the back-mixed Berty reactor (internally goldplated) in a quasi-static mode. This involved manually closing valves to stop all flow of reactants into the reactor. Flow of gas out of the reactor was controlled by a pressure-actuated valve whose leakage rate proved to be low (0.5–3.0 STP 1/hr). Several experiments were conducted with the reactor sealed in this manner and maintained at reaction conditions of pressure and temperature. Reactant gases were added as needed by manual manipulation in order to maintain the total pressure near the desired nominal value. Liquid samples were collected by purging small volumes of gas from the reactor through the condenser in the product gas line.

Three catalysts were studied in both the low space velocity and the quasi-static operating modes. Many of these esperiments attempted to study the product distribution obtained at low synthesis temperatures and low reaction rates. Moreover, the major objective was to study the product distribution at conditions of high conversion. The relevant catalysts studies were: (1) 5% rhodium on Davison 59 silica gel; and (2) powdered, bulk rhodium metal prepared in situ reduction of rhodium oxyhydrate (prepared by Soufi's method for making "Catalyst D", page 23 of dissertation). The rhodium oxyhydrate was charged to the reactor in a "jelly-roll" of glass wool and stainless steel screen.

The silica-gel-supported rhodium catalyst was studied at 2500 psi and temperatures of 200°, 250°, 300°, and 325° C. Several (7 out of 34) of the liquid product samples contained measurable quantities of hydrocarbon

TABLE VIII

| Test No. | Temp. °C | Products (grams) | | | | | | | % Efficiency | | | |
|---|---|---|---|---|---|---|---|---|---|---|---|---|
| | | H₂O | Methane | Acetic Acid | Ethanol | Total[a] Aldehydes | Total[c] Esters | Other[b] Alcohols | Methane | Acetic[d] Acid | Ethanol[d] | Acetaldehyde |
| 13 | 300 | 4.2 | 0.29 | 1.82 | 0.02 | 0.31 | 0.04 | 0.01 | 18 | 64 | 1 | 10 |
| 14 | 300 | 4.0 | 0.39 | 3.75 | 0.04 | 0.72 | 0.20 | 0.02 | 12 | 65 | 2 | 11 |
| 15 | 300 | 4.0 | 0.26 | 3.81 | 0.04 | 0.72 | 0.33 | 0.02 | 8 | 68 | 2 | 11 |
| 16 | 325 | 3.6 | 0.33 | 4.23 | 0.06 | 0.58 | 0.28 | 0.02 | 10 | 71 | 3 | 9 |
| 17 | 325 | 4.6 | 0.69 | 5.62 | 0.17 | 1.64 | 0.74 | 0.02 | 12 | 57 | 6 | 15 |
| 18 | 325 | 6.6 | 0.63 | 8.34 | 0.22 | 2.20 | 1.35 | 0.04 | 8 | 62 | 6 | 15 |
| 19 | 325 | 3.8 | 0.96 | 4.67 | 0.08 | 0.47 | 0.42 | 0.02 | 23 | 62 | 3 | 6 |
| 20 | 350 | 6.4 | 0.96 | 7.69 | 0.46 | 2.47 | 2.19 | 0.05 | 11 | 54 | 10 | 16 |
| 21 | 350 | 6.1 | 0.62 | 2.47 | 1.72 | 0.40 | 1.69 | 0.42 | 13 | 40 | 33 | 5 |
| 22 | 350 | 6.6 | 0.59 | 1.42 | 3.20 | 0.34 | 1.52 | 0.92 | 11 | 25 | 47 | 4 |
| 23 | 350 | 5.1 | 0.55 | 0.88 | 1.99 | 0.19 | 0.89 | 0.50 | 16 | 24 | 46 | 4 |
| 24 | 325 | 6.3 | 0.63 | 1.38 | 2.25 | 0.24 | 0.78 | 0.68 | 11 | 26 | 44 | 4 |
| 25 | 325 | 3.7 | 0.71 | 0.78 | 0.72 | 0.07 | 0.09 | 0.21 | 39 | 24 | 28 | 3 |
| 26 | 325 | 3.99 | 1.09 | 4.24 | 0.05 | 1.57 | 0.41 | — | 22 | 49 | 3 | 16 |
| 27 | 3125 | 3.15 | 0.68 | 6.08 | 0.10 | 1.86 | 0.79 | — | 11 | 58 | 5 | 14 |
| 28 | 325 | 4.14 | 0.67 | 6.64 | 0.09 | 1.32 | 0.56 | — | 12 | 65 | 4 | 12 |
| 29 | 325 | 1.56 | 0.20 | 5.37 | 0.06 | 1.01 | 0.48 | — | 15 | 64 | 4 | 11 |
| 30 | 325 | 3.72 | 0.62 | 6.28 | 0.07 | 1.22 | 0.68 | — | 11 | 65 | 5 | 11 | a. predominately acetaldehyde with lesser amounts of propionaldehyde, butlyaldehyde and crotonaldehyde.
b. methanol and propanol.
c. predominately ethyl acetate with lesser amounts of methyl, propyl and butyl acetates
d. includes acetic acid on ethanol as esters.

oil. Here too the product distributions were generally similar to the usual experience with two-carbon products greatly exceeding longer chain organics. However, in two cases (out of 34), the yield of heavies exceeded the yield of two-carbon products, and in several more cases the yield of heavies was more than 20% of the yield of two-carbon products (weight basis). In general, these results provide some support for the original hypothesis that longer chain products result from long contact times and high conversions.

Unsupported rhodium was studied at 2500 psi and temperatures of 160°, 200°, 300°, and 325° C. Quasi-static experiments were made at 300° and 325° C. The experiments at 160° and 200° C. produced only very small quantities of products and these products contained much more two-carbon products than heavies. The experiments at 300° and 325° C. were distinctly different. The productivities were greater, and the quantities of heavies were almost always substantially (2- to 8-fold) greater than the quantities of two-carbon products. Five out of 22 samples contained measurable quantities of oil. The proportion of heavies was very substantially less than that reported by Soufi, however. It would appear that the form in which the rhodium is introduced is apparently not the only factor which determines the product distribution. Comparison of these results to those reported by Soufi implies that either reaction conditions (notably temperature, GHSV, and extent of conversion) or other unidentified factors also strongly influence the product distribution.

The Table below summarizes results in a somewhat over-simplified form.

procedure in experiments A through J were the same as those used in the previous Series above. All of the experiments A-J were made using a fresh 60 gram sample of Catalyst D above, i.e., 5 percent rhodium on Davison$^{TM}$, grade 59, silica gel, at 2,500 psig, a feed gas composition of 3 moles of carbon monoxide per mole of hydrogen and a feed gas rate of 450 liters/hour. The CO feed gas of experiments A through K contained about 3 to 5 mole percent $CO_2$.

In each experiment the reaction was allowed to proceed for one hour before a sample was taken for analysis or the reactor was shut down overnight. Experiments A and B were consecutive one hour runs, i.e., there was no shut down of the reactor after the first sample but the reaction was allowed to proceed for one more additional hour before sample B was taken. After experiment B, the reactor was shut down and the catalyst was stored overnight in the reactor at 250° C., under a 600 psig $H_2$ atmosphere and a slight $H_2$ flow through the reactor before being used in experiment C. Experiments C through F were four consecutive one hour runs. After experiment F, the catalyst was removed from the reactor and heated at 350° C. in air for 2.5 hours and then reduced overnight in the reactor at 200° C. and a $H_2$ pressure of 500 psig. The catalyst from experiment F was then used to make the consecutive one hour runs of experiments G and H. A fresh sample of Catalyst D above was used on the two consecutive one hour runs of experiments I and J.

Auger analysis of the used catalyst of experiment F showed sulfur at levels of 10 to 15 atomic percent of that surface rhodium. The reason for the presence of sulfur is presently unaccounted for.

TABLE XI

| Experiment No. | Temp. °C. | Total Product gms./hr. | Product (gms./hr.) $H_2O$ | $CH_3COOH$ | $CH_4$ | Percent Efficiency $CH_3COOH$ | $C_2H_5OH$ | $CH_3\overset{O}{\overset{\|}{C}}-H$ | $CH_4$ | Productivity* | Ratio of Moles of $CH_3COOH/$ to $C_2H_5OH$ |
|---|---|---|---|---|---|---|---|---|---|---|---|
| A | 250 | 5.8 | 3.5 | 1.96 | 0.2 | 67 | 1 | 12 | 13 | 0.70 | 82 |
| B | 250 | 6.3 | 2.7 | 2.78 | 0.2 | 64 | 1 | 11 | 9 | 0.97 | 52 |
| C | 275 | 8.9 | 7.0 | 1.70 | 1.1 | 42 | .1 | 7 | 50 | .60 | 284 |
| D | 275 | 6.8 | 4.5 | 2.11 | .56 | 59 | 1 | 9 | 29 | .74 | 70 |
| E | 275 | 6.6 | 4.1 | 2.23 | .45 | 64 | 1 | 9 | 24 | .78 | 53 |
| F | 275 | 4.0 | 2.3 | 1.69 | .46 | 61 | 1 | 5 | 31 | .59 | 47 |
| G | 250 | 7.0 | 5.25 | 1.61 | .34 | 46 | 1 | 5 | 24 | .56 | 69 |
| H | 250 | 3.7 | 2.67 | 0.94 | .21 | 59 | .5 | 2 | 28 | .33 | 150 |
| I | 250 | 22.0 | 9.4 | 10.83 | .73 | 72 | 1 | 11 | 9 | 3.8 | 75 |
| J | 250 | 17.6 | 5.8 | 10.64 | 1.07 | 71 | 1 | 9 | 13 | 3.7 | 74 |
| K | 250 | 9.8 | 4.1 | 5.48 | .64 | 76 | 1 | 5 | 16 | 1.9 | 95 |

*Productivity as used here means lbs. Acetic acid/cu. ft./hour.

| Comparison of Product Distributions | |
|---|---|
| Catalyst | $C_3^+/C_2$ (weight ratio)*** |
| 5% Rh on Davison TM -Grade 59 Silica gel | ca. 0.5 to 0.05* |
| Rh black (UCC) | ca. 5.* |
| Rh black (Soufi Thesis) | ca. 170.** |

*ca. 2$H_2$ per CO at 2500 psi. Temperature ca. 300° C.
**2$H_2$ per CO at 7500 psi. Temperature 160° C.
***The ratio of the sum of the weights of three and higher number carbon products and the sum of the weights of acetaldehyde, ethanol and acetic acid.

SERIES E

This series illustrates preliminary tests, utilizing a silver plated reactor of the type employed in the previous Series, to study the effect of reaction temperature on product distribution.

Except for the silver plating of the reactor, and for the following recited conditions, the equipment and

What is claimed is:

1. In a process for the reaction of a synthesis gas containing carbon monoxide and hydrogen in the presence of a hydrogenation catalyst, the improvement whereby oxygenated hydrocarbon products of two carbon atoms are selectively produced, which comprises continuously contacting said synthesis gas with a heterogeneous catalyst comprising rhodium metal and at reaction conditions correlated to achieve such product in efficiencies, based on carbon consumption, in excess of 10% and obtain the formation of acetic acid, ethanol, and/or acetaldehyde in an amount which is at least about 50 weight percent of the two or more carbon atom compounds obtained by the reaction, which reaction conditions include a temperature within the range of about 150°–450° C., a pressure within the range of about 15–10,000 psig, a space velocity of the synthesis gas in excess of about $10^3$ GHSV and a mole ratio of hydrogen to carbon monoxide within the range of 20:1 to 1:20.

2. Process of claim 1 wherein said reactive conditions include a temperature within the range of about 250°–350° C., a pressure within the range of about 300–5,000 psig, and a mol ratio of hydrogen to carbon monoxide within the range of about 5:1 to 1:5.

3. Process of claim 1 wherein said rhodium metal is present on a support in amounts within the range of about 0.1 to about 25 weight percent based on the combined weight of the metal and support.

4. Process of claim 1 wherein said support is selected from the group consisting of alpha alumina, gamma alumina, and silica gel.

5. Process of claim 1 wherein said space velocity is within the range of about $10^4$ to $10^6$ GHSV.

6. Process of claim 1 wherein said two carbon atom oxygenated hydrocarbons are at least (10) 50 percent of the reacted carbon atoms.

* * * * *

UNITED STATES PATENT AND TRADEMARK OFFICE
CERTIFICATE OF CORRECTION

PATENT NO. : 4,246,186
DATED : January 20, 1981
INVENTOR(S) : Madan M. Bhasin et al.

It is certified that error appears in the above—identified patent and that said Letters Patent is hereby corrected as shown below:

Table VI at Columns 9-10, line 26, Test No. 14 under heading Rate to $C_2$ Products, lb/cf/hr, "0.026" should read -- 0.025 --.

Table VI at Columns 9-10, line 33, Test No. 23 under heading GHSV $hr^1$ (h), "8800" should read -- 8300 --.

Table VII at Columns 13-14, line 15, Test No. 7 under heading Methanol, "1.12" should read -- 1.21 --.

Table VII at Columns 13-14, line 20, Test No. 12 under heading Ethanol, "0.04" should read -- 0.40 --.

At Column 15, line 4, "of Table VII" should read -- of Table VIII --.

Table VIII at Columns 15-16, line 63, Test No. 27 under heading Temp. °C, "3125" should read -- 325 --.

Table VIII at Columns 15-16, line 63, Test No. 27 under heading $H_2O$, "3.15" should read -- 5.15 --.

Table VIII at Columns 15-16, line 64, Test No. 28 under heading $H_2O$, "4.14" should read -- 4.34 --.

UNITED STATES PATENT AND TRADEMARK OFFICE
CERTIFICATE OF CORRECTION

PATENT NO. : 4,246,186
DATED : January 20, 1981
INVENTOR(S) : Madan M. Bhasin et al.

It is certified that error appears in the above—identified patent and that said Letters Patent is hereby corrected as shown below:

Table VIII at Columns 15-16, line 65, Test No. 29 under heading $H_2O$, "1.56" should read -- 3.56 --.

Claim 6, at Column 20, line 9, "hydrocarbons are at least (10) 50 percent of" should read -- hydrocarbons are at least 50 percent of --.

Signed and Sealed this

Eighth Day of September 1981

[SEAL]

Attest:

Attesting Officer

GERALD J. MOSSINGHOFF
Commissioner of Patents and Trademarks